US009110001B2

(12) United States Patent
Green et al.

(10) Patent No.: US 9,110,001 B2
(45) Date of Patent: Aug. 18, 2015

(54) METHOD FOR TAGGING REFERENCE MATERIALS OF INTEREST IN SPECTROSCOPIC SEARCHING APPLICATIONS

(75) Inventors: Robert L. Green, Haverhill, MA (US); Michael D. Hargreaves, Lawrence, MA (US); Craig M. Gardner, Belmont, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 568 days.

(21) Appl. No.: 13/540,152

(22) Filed: Jul. 2, 2012

(65) Prior Publication Data

US 2014/0005980 A1 Jan. 2, 2014

(51) Int. Cl.
*G06F 17/00* (2006.01)
*G01N 24/08* (2006.01)
*G06F 17/18* (2006.01)
*G01R 33/46* (2006.01)
*G01N 21/64* (2006.01)
*G07D 7/12* (2006.01)
*G05B 23/02* (2006.01)

(52) U.S. Cl.
CPC .............. *G01N 24/08* (2013.01); *G01N 21/643* (2013.01); *G01R 33/4625* (2013.01); *G06F 17/18* (2013.01); *G07D 7/122* (2013.01); *G01N 24/084* (2013.01); *G01N 24/085* (2013.01); *G05B 23/0254* (2013.01)

(58) Field of Classification Search
CPC ..... G06F 17/18; G06K 9/00536; G06Q 10/04
USPC .......................... 702/181, 189, 183, 179, 127
See application file for complete search history.

(56) References Cited

U.S. PATENT DOCUMENTS

| 6,424,745 | B1 * | 7/2002 | Hansen et al. | 382/191 |
| 7,698,098 | B2 * | 4/2010 | Ritter et al. | 702/179 |
| 2004/0058385 | A1 | 3/2004 | Wishart | |
| 2011/0042559 | A1 * | 2/2011 | Klepel | 250/282 |
| 2011/0246145 | A1 * | 10/2011 | Multari et al. | 703/2 |
| 2011/0246414 | A1 * | 10/2011 | Klepel | 706/54 |
| 2012/0072122 | A1 * | 3/2012 | Schweitzer et al. | 702/19 |

FOREIGN PATENT DOCUMENTS

| EP | 2508909 A2 | 10/2012 |
| GB | 2472908 A | 2/2011 |

OTHER PUBLICATIONS

Jeong, Jaesik et al., "An empirical Bayes model using a competition score for metabolite identification in gas chromatography mass spectrometry," BMC Bioinformatics Biomed Central Ltd. UK, vol. 12, 2011.

Zhang et al., "Profound: An expert system for protein identification using mass spectrometric peptide mapping information," Analytical Chemistry, American Chemical Society, US, vol. 72, No. 11, Jun. 1, 2000.

* cited by examiner

*Primary Examiner* — John Breene
*Assistant Examiner* — Mohammad K Islam
(74) *Attorney, Agent, or Firm* — William R. McCarthy, III

(57) ABSTRACT

A method, apparatus and computer program product for tagging reference materials of interest in spectroscopic searching applications is presented. A reference list of materials to be considered as part of a final analysis of a spectroscopic analysis of a sample material is generated. A watchlist of at least one material to be retained for a final analysis of the spectroscopic analysis of a sample material is provided. A final analysis of the sample material is preformed using the watchlist of at least one material and the reference list of materials. A determination is then made regarding whether a spectrum of the sample material matches at least one spectrum of materials on the watchlist and on the reference list.

33 Claims, 3 Drawing Sheets

METHOD FOR TAGGING REFERENCE MATERIALS OF INTEREST IN SPECTROSCOPIC SEARCHING APPLICATIONS

BACKGROUND

Contemporary analytical instrumentation is frequently capable of producing multi-channel data which can be related to the concentration of analyte in a sample (referred to herein as quantitative analysis) or the identity of one or more materials present in a sample (referred to herein as qualitative analysis). Examples of instruments capable of producing such data include Infrared and Raman spectrometers, Mass spectrometers, X-ray Fluorescence (XRF) spectrometers, and Nuclear Magnetic Resonance (NMR) Spectrometers. Within the scope of qualitative analysis, there are several types of assessments that can be performed.

One type of qualitative analysis assessment is authentication which examines whether the measured instrument response is consistent with one or more reference library signatures for a specific material of interest. Said differently, this type of analysis aims to determine if the test material spectrum is consistent with a genuine substance. Examples of applications where authentication is performed include evaluation of raw materials received from a supplier to determine whether the correct ones were provided, examination of a tablet to determine whether it is genuine or counterfeit, and analysis of a material to determine whether it has been adulterated, spoiled, etc.

Another type of qualitative analysis assessment is screening which evaluates whether at least a subset of features in the measured instrument response correspond to one or more specific substances of interest. This type of assessment evaluates whether the test material appears to contain a particular substance. Screening can be used by those with a very small set of analytes of particular interest, such as narcotics, explosives, or materials of environmental concern. In a screening assessment it is not necessary to determine the identity of materials that are not in a watch list. For example, it may be important to know whether a children's toy contains lead but it is not necessary understand what type of plastic, wood, or metal are present.

Yet another type of qualitative analysis assessment is identification which is performed by scouring a library of known materials and looking for similarities between the unknown instrument response and the stored responses for known materials (or combinations of stored responses for known materials). Such an assessment assumes the user does not know what they are testing for, and thus wants to know "what is this material?". Computer-aided identification is frequently referred to as "automated spectral searching", and is frequently used in scenarios such as hazardous material (hazmat) calls and laboratory investigations.

From the above descriptions, it can be noted that the authentication problem is designed for users with a very specific need (those who know exactly what they are testing for). On the other hand, the screening and identification problems are much less bounded. Given the extremely broad applicability that identification apparatus provides, it may be noted that they can be used to identify any analyte that a screening apparatus might be configured to detect, plus many more. There are two principal advantages of screening that compel users to forgo the broad applicability provided by identification: screening algorithms can typically be configured to have higher detection rates and lower limits of detection than identification algorithms, and a screening apparatus can be configured to provide a user with visual and/or audio cues that a specific material of interest has been detected. When an identification application detects a material, it does not call specific materials out as more important or concerning than other materials.

SUMMARY

Conventional mechanisms such as those explained above suffer from a variety of deficiencies. As might be expected, it is typically considered more challenging to accurately perform automated analysis of an unknown mixture than it is to accurately identify pure component samples. Modern reference databases in use today frequently contain more than 10,000 reference spectra, and many mixture procedures attempt to fit four or more mixture components. The number of possible mixture solution candidates that can be evaluated can be expressed by "n choose k" which is expressed by the formula:

$$N = \frac{n!}{k!(n-k)!}$$

wherein N is the number of possible mixture solution candidates, n is the number of available reference spectra, and k is the maximum number of mixture components that are simultaneously fit. For a reference library with 10,000 items, the number of possible mixture combinations scales rapidly with the number of components that are simultaneously fit:

| n | k | N |
| --- | --- | --- |
| 10,000 | 2 | $4.9995 \times 10^7$ |
| 10,000 | 3 | $1.6662 \times 10^{11}$ |
| 10,000 | 4 | $4.1642 \times 10^{14}$ |
| 10,000 | 5 | $>1 \times 10^{15}$ |

As shown above even if the analysis is limited to looking for mixtures of only two components, there are more than $10^7$ possible solutions when a 10,000 item reference library is used. Due to the extremely large number of possible mixture combinations that can be formed when working with large reference databases used in automated spectral searching applications, it is common to perform a rapid calculation that can be used to down select the library to a more manageable number of entries. Though such procedures are designed to retain the reference candidates most likely to be represented in the unknown spectrum, the procedure is never perfect. Therefore, one common failure mode of automated mixture identification is that an analyte which is present in the unknown is dismissed from consideration prior to examination, by the slower, more precise final analysis algorithms.

In contrast to general identification algorithms, screening approaches require that the analytes of interest are specified ahead of time. Frequently, potential interferents are also specified ahead of time. Thus, the reference spectrum database used for analysis is already quite small and there is no need to do a down selection. As such, screening algorithms do not suffer from a false negative condition associated with early dismissal of target compounds prior to analysis by final analysis algorithm.

Embodiments of the invention significantly overcome such deficiencies and provide mechanisms and techniques that enable tagging reference materials of interest in spectroscopic searching applications.

Disclosed herein is a method that combines the broad applicability provided by identification devices (many thousands of possible identification results) with the improved detection and reporting capabilities of screening devices. Briefly, the methodology involves providing the ability for a user to tag materials and create a watchlist within a database or library. The watchlist substances are materials that the user either has reason to believe might be present in the sample or are materials of such concern that the user wants to check for them in detail even if they have no prior information to suggest that they are present. The watchlist materials are handled by the algorithms in such a way that the limit of detection for these materials is improved. Additionally, watchlist materials are treated preferentially in the device display to unambiguously indicate to the user when a material of interest has been detected.

In a particular embodiment of a method for tagging reference materials of interest in spectroscopic searching applications, the method includes obtaining a candidate list of reference materials to be considered during final analysis of a spectroscopic analysis of a sample material. The method also includes providing a watchlist of at least one material to be retained for a final analysis of the spectroscopic assessment of a sample material. Additionally, the method includes performing a final analysis of the sample material using the watchlist of at least one material and the reference list of materials and determining whether a spectrum of the sample material matches at least one spectrum of materials on the watchlist and on the reference list.

Other embodiments include a computer readable medium having computer readable code thereon for providing tagging reference materials of interest in spectroscopic searching applications. The computer readable medium includes instructions for obtaining a reference list of materials to be considered as part of a final analysis of a spectroscopic analysis of a sample material. The computer readable medium also includes instructions for providing a watchlist of at least one material to be retained for a final analysis of the spectroscopic analysis of a sample material. Additionally, the computer readable medium includes instructions for performing a final analysis of the sample material using the watchlist of at least one material and the reference list of materials and instructions for determining whether a spectrum of the sample material matches at least one spectrum of materials on the watchlist and on the reference list.

Still other embodiments include a computerized device (e.g., a spectroscopic system) configured to process all the method operations disclosed herein as embodiments of the invention. In such embodiments, the computerized device includes a memory system, a processor, communications interface in an interconnection mechanism connecting these components. The memory system is encoded with a process that allows the user to tag reference materials of interest in spectroscopic searching applications as explained herein that when performed (e.g. when executing) on the processor, operates as explained herein within the computerized device to perform all of the method embodiments and operations explained herein as embodiments of the invention. Thus any computerized device that performs or is programmed to perform up processing explained herein is an embodiment of the invention.

Other arrangements of embodiments of the invention that are disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing tagging reference materials of interest in spectroscopic searching applications as explained herein. The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as software and hardware, or as hardware and/or circuitry alone. Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
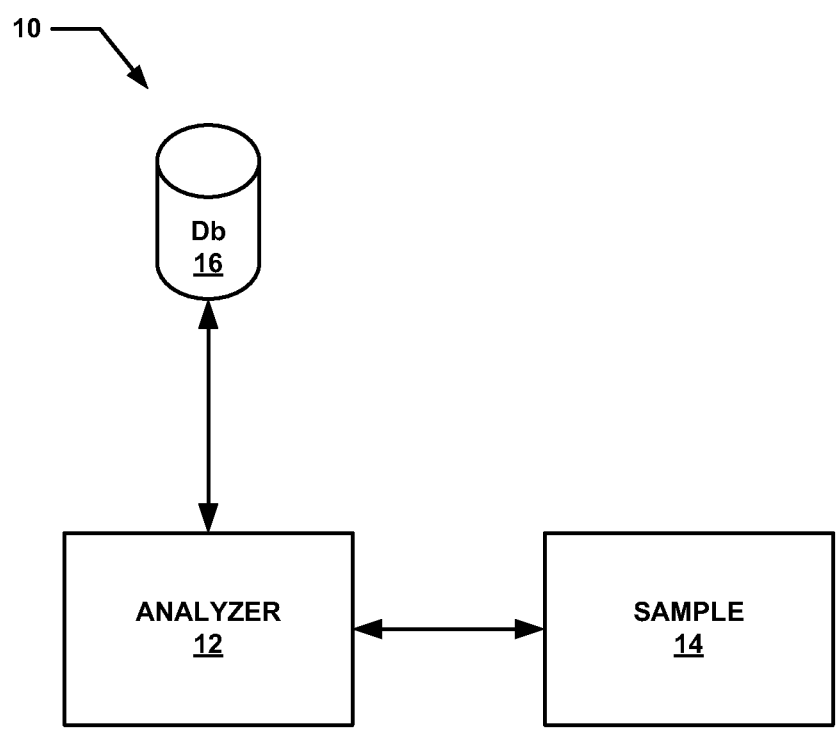
FIG. 1 depicts a high-level bock diagram of a system for tagging reference materials of interest in spectroscopic searching applications in accordance with embodiments of the invention.

The embodiments set forth below represent the necessary information to enable those skilled in the art to practice the invention and illustrate the best mode of practicing embodiments of the invention. Upon reading the following description in light of the accompanying figures, those skilled in the art will understand the concepts of the invention and recognize applications of these concepts not particularly addressed herein. It should be understood that these concepts and applications fall within the scope of the disclosure and the accompanying claims.

The preferred embodiment of the invention will now be described with reference to the accompanying drawings. The invention may, however, be embodied in many different forms and should not be construed as limited to the embodiment set forth herein; rather, this embodiment is provided so that this disclosure will be thorough and complete, and will fully convey the scope of the invention to those skilled in the art. The terminology used in the detailed description of the particular embodiment illustrated in the accompanying drawings is not intended to be limiting of the invention. In the drawings, like numbers refer to like elements.

Computer-aided identification, or "automated spectral searching" algorithms have been in use for a number of years. Early approaches include procedures based on peak table comparisons and various full spectrum searching methods. More recently, probabilistic based methods and procedures for automatic mixture analysis have also been introduced.

One aspect of the presently disclosed method and apparatus for tagging reference materials of interest in spectroscopic searching applications is to ensure that tagged items of interest (watchlist materials) are unlikely to be prematurely rejected from consideration by the final analysis algorithms. In conventional spectrum searching applications (which do not allow users to tag items of interest), no preference is given to specific materials of interest during the down selection process. Thus, the unknown spectrum is rapidly compared to each material from the reference database (usually using a compressed form of data such as peak tables), and a rank ordered list is generated such that the top m items are retained. This does not allow the user's knowledge of the scenario (e.g. they may have other intelligence suggesting that a particular material of interest might be present) to influence the outcome of the analysis.

In a particular embodiment of the current invention, all items on the watchlist are automatically retained for consideration by the final analysis algorithms. This ensures that any material that the user is concerned about or believes might be present will receive full consideration by the analysis algorithms. For situations where time constraints do not permit all watchlist materials to be considered by the final analysis algorithms, another embodiment of the invention is to preferentially weight the watchlist during the down selection procedure. There are many approaches one could take to accomplish this. For example, one could perform the typical rapid analysis for down selection and retain the top m non-watchlist materials and the top k watchlist materials such that the total number of materials retained (m+k) can be evaluated in the desired period of time. Alternately, one could determine a threshold for each watchlist material above which the material is automatically retained independent of its ranking relative to the full reference library and below which it is retained only if it ranks highly relative to the library. One skilled in the art will recognize that other means of preferentially retaining watchlist materials during down selection could easily be devised.

Once a plurality of possible components that might be present in the sample has been determined, analysis is performed using final analysis identification algorithms. Within the context of the present invention, the plurality of components chosen to submit for final analysis will always contain both watchlist and non-watchlist materials. Using the conventional approach, there is no watchlist so materials the user believes might be present (e.g. narcotics, explosives, chemical weapons) are only considered by the final analysis algorithms if they have passed through the initial down selection procedure. In either case, the next step is to evaluate whether the unknown spectrum is a match to one or more pure reference spectra or a combination of reference spectra. For the analysis to be truly automated, goodness of fit thresholds must be set in the algorithm to determine which component(s), if any, will be reported. In an automated analysis, the need to set reporting thresholds is universal and does not depend on which type of analysis algorithm used.

Selection of the reporting threshold has a direct impact on the trade-off between true positive rate (TPR) and false positive rate (FPR) of the search appliance. In a typical unknown identification scenario, such as a hazmat call, special consideration is made to ensure that the FPR is kept low. This prevents the user from acting on information that may be ambiguous and allows them to focus time and efforts on other assessments that may provide more definitive information. In a screening scenario the reporting thresholds are often set to maximize TPR, even at the expense of FPR (often when there is a positive result, there is a second confirmatory test that can be performed to mitigate potential false positives).

Based on the considerations just discussed, another reason that screening algorithms are capable of providing better detection rates than standard identification algorithms is that the criteria used to set reporting thresholds (TPR versus FPR) is optimized differently. In the context of the present invention, the watchlist represents materials that the user either has reason to believe might be present in the sample or are of such grave concern that maximization of the TPR, potentially at expense to the FPR, is considered acceptable. Thus, one embodiment of the present invention is that reporting thresholds for watchlist materials can be set differently than non-watchlist materials as to maximize the probability of detecting those substances.

As noted above, some final analysis algorithms use probabilistic based methods. Such algorithms can incorporate 'prior probabilities' and utilize Bayes theorem to determine the exclusive probability that the measured material is a representation of one library entry versus another, often termed the "posterior probability". When no extra intelligence (i.e., information beyond the measured instrument response such as color, pH, or phase of matter) is available at the time of measurement, no prior preference exists for any particular library component (a condition often termed "flat prior" in the probability literature). As previously noted, when a watchlist has been provided by a user this is an indication that they believe a particular set of materials are more likely to be present in the sample than other sets of materials. As such, one embodiment of the current invention is to provide preferred prior probabilities for watchlist items relative to non-watchlist items when probabilistic based methods are in use.

As described above, screening algorithms are designed to determine whether at least a subset of features in the measured instrument response correspond to one or more substances of interest. Correspondingly, in screening it is not necessary to determine the identity of materials that are not in the watchlist. In contrast, identification algorithms are designed to identify all of the features in an unknown spectrum. If an unknown spectrum contains features from a material that is not represented in the reference library database, this task becomes impossible. Thus, screening algorithms enhance detection capability in scenarios where the unknown sample contains an interferent not represented in the reference library database.

An additional embodiment of the present invention is to introduce a dual algorithm capability wherein in a first step the modified identification algorithm just summarized is utilized. If an acceptable solution is found that meets the combined watchlist and non-watchlist reporting criteria, it is reported. If an acceptable solution is not found, a second step is undertaken using screening algorithms that do not require all features of the unknown spectrum to be accounted for.

In addition to detection considerations, one other advantage of screening apparatus is that they are often configured to provide the user with visual and/or audio cues that a specific material of interest has been detected. Though some identification systems are capable of indicating that a general category threat (e.g. explosive, narcotic, etc.) has been identified, there is no general identification system that highlights when a specific materials of interest (e.g., Nitroglycerin, cocaine, etc.) has been detected.

In a particular embodiment of the current invention an identification result that contains a watchlist material is distinguished with a special icon when a watchlist material has been detected. In an alternate embodiment of the current invention a message to the user, e.g., "watchlist material detected" could also be used to convey this information to the user. In either case, the user is provided a clear indication that a "special" material has been detected. This removes subjectivity from the interpretation of the results and does not require that the user independently assess whether an identified material is of special concern.

As described above, the current invention utilizes a combined algorithm architecture incorporating some features of identification algorithms with some features of screening algorithms in order to enhance the probability of detection and results display for user defined watchlist materials. Since the watchlist is user defined, the approach is extremely flexible and can be utilized for a wide variety of applications important to different user groups (e.g. narcotics, explosives, chemical weapons, toxic industrial chemicals, etc.). It is also assumed that a single user group may want to configure the device with different watchlists to suit more than a single "mission scenario". There are several embodiments of this invention to assist in this consideration.

Under a particular embodiment of this invention, the user is given an opportunity to name any watchlist that is created. Using this approach, one possible embodiment of the device is to configure it such that the user can select between multiple watchlists that are simultaneously present on a device. Under a different embodiment, only a single watchlist is allowed on the device at any given time but there is capability to switch what watchlist is present (through simple import/export functionality).

The import/export functionality just described is an important general embodiment of this invention. In addition to allowing users to switch between different watchlists on a single device, this functionality allows users with multiple devices to create a watchlist configuration on one device and then export the watchlist configuration from that device such that it can be imported onto other device (e.g., this is a form of fleet management).

Another embodiment of this approach is that watchlists can be built using a combination of reference data inherent to the application (e.g., on a handheld scanner this might correspond to factory library items), and reference data provided by the user (e.g. user added library items). When a watchlist is exported, it is captured such that any user provided reference data is exported along with the watchlist configuration (which is otherwise made up of indices that represent which items from the reference database have been tagged).

In one embodiment of the invention, watchlist reporting thresholds are hard-coded or otherwise self-determined by the processor, while in another embodiment the reporting thresholds could be set by a system administrator.

In still another embodiment, the tagging feature is used to help determine the appropriate measurement settings do be used in collection of the data. Two specific cases would include Raman and Infrared spectroscopy. In these techniques, the signal strength of for every material is different. In Infrared the signal strength might be described based on the absorption coefficient, while Raman practitioners would discuss the Raman cross section. Generally speaking, materials with a lower signal strength are more difficult to detect, especially in mixtures, than materials with a high signal strength. This is because the spectrum from a mixture containing a substance with a high signal strength and a second substance with a low signal strength will be dominated by the material corresponding to the high signal strength. Said differently, the spectral contribution from the material with the low signal strength may be approaching the noise level in the measurement. If one were doing a measurement to look for a tagged item that is known to have a very weak signal, one approach to improve the limit of detection would be to alter the scan settings so that features from the tagged item are more likely to be above the noise level of the measurement (if the substance is present). Thus, an additional embodiment of this invention is to target the scan settings (desired signal to noise ratio, etc.) based on known spectral characteristics (e.g. signal strength) for materials on the watchlist. By "scan setting" in this context is referenced any setting of a device used to obtain the spectroscopic analysis of the sample material. For example, this can include intensity, duration, or wavelength of the source (such as a light source) used to interrogate the sample, gain or other settings of a detector in the device or for signal processing of detected signal, or the number of scans performed. When a spectrum of a sample does not match at least one spectrum of materials on the watchlist or reference list, any embodiment of the present invention can optionally include then performing additional scans at the same or different scan settings.

A particular example will now be discussed. Referring to FIG. 1, a spectroscopic system 10 is shown. The system 10 includes an analyzer 12 in communication with a sample 14. Analyzer 12 is also in communication with a database 16. In general, the analyzer 12 may perform a general identification test looking through tens of thousands of possible substance matches stored in database 16. Analyzer 12 may also be used in a screening type test, looking through one to tens of substances. Some users want the general ability to identify tens of thousands of materials, but they also might have a subset of substances that are of particular interest. The general identification test may take a long time whereas the screening tests take much less time.

In the described example, consider the assessment of an unknown tablet sample. The end user is interested in knowing the identity of the major components of the unknown material, and for this particular example they are also interested in determining which, if any, controlled substances are present. Further consider a tablet material such as Ritalin, which is formulated such that the active (e.g., Ritalin hydrochloride, also known as methylphenidate hydrochloride) is at much lower concentration than the primary excipients (e.g. lactose and starch). Not surprisingly, when such a tablet is measured the spectroscopic features corresponding to the Ritalin hydrochloride are much weaker than those corresponding to the primary excipients (lactose and starch). If the tablet is measured and a conventional search apparatus is applied, it is likely that lactose and starch can be identified as they contribute enough signal to the data that conventional down selection, reporting thresholds, etc. still allow detection of these analytes. In contrast, the conventional search apparatus may not be able to detect Ritalin because the corresponding features in the unknown spectrum are weak enough that the corresponding reference spectrum may be eliminated during a downselection from a library of more than 10,000 entries to a smaller list that is passed onto the final analysis algorithms. Using a conventional search apparatus even if Ritalin hydrochloride is evaluated by the final analysis algorithms, there is still the possibility that it would not be detected if the contribution of the Ritalin to the unknown spectrum does not meet the reporting thresholds of the conventional identification algorithm. Consider instead what happens when the unknown spectrum is analyzed using the method disclosed herein which in this example utilizes a reference library of more than 10,000 items wherein controlled substances have been tagged and added to a watchlist. Under this scenario, Ritalin is included in the watchlist items, which ensures that it will be considered by the final analysis algorithms. Furthermore, when analyzing a material comprised of as mixture of several materials, each component can be assigned a weighting or fit value. If the weight of a material within a fit is too low, then the material is not reported. In this example, the reporting threshold for lactose and starch are left alone, since these items are not present on the watchlist. In contrast, for Ritalin or other controlled substances on the watchlist, a lower reporting threshold can be used such that the presence of these materials will be reported, even if only a very small percentage of the unknown spectrum is described by one or more of these materials.

Figure 2:
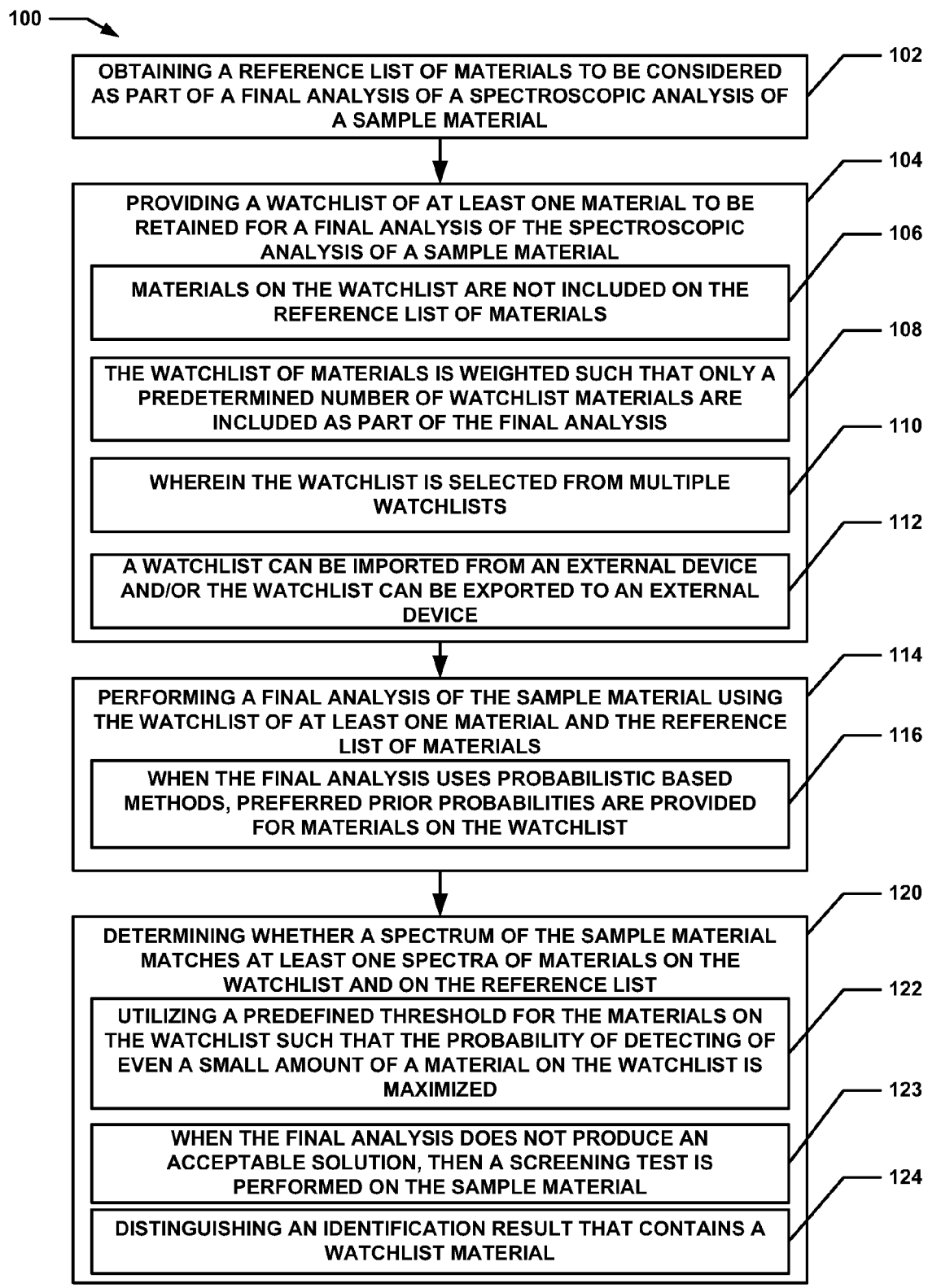
FIG. 2 depicts a flow diagram of a particular embodiment of a method for tagging reference materials of interest in spectroscopic searching applications in accordance with embodiments of the invention.

A flow chart of a particular embodiment of the presently disclosed method is depicted in FIG. 2. The rectangular elements are herein denoted "processing blocks" and represent computer software instructions or groups of instructions. Alternatively, the processing blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. It should also be noted that certain processing blocks may be optional. These optional processing blocks include processing blocks, 106, 108, 110, 112, 116, 122 123 and 124.

Method 100 begins with processing block 102 which discloses generating a reference list of materials to be considered as part of a final analysis of a spectroscopic analysis of a sample material.

Processing block 104 states providing a watchlist of at least one material to be retained for a final analysis of the spectroscopic analysis of a sample material. Thus is done to ensure that tagged items of interest (watchlist materials) are unlikely to be prematurely rejected from consideration by the final analysis algorithms.

Processing block 106 recites materials on the watchlist are not included on the reference list of materials. Processing block 108 discloses the watchlist of materials is weighted such that only a predetermined number of watchlist materials are included as part of the final analysis. This is used for situations where time constraints do not permit all watchlist materials to be considered by the final analysis algorithms. One approach for this embodiment of the invention is to preferentially weight the watchlist during the down selection procedure. There are many approaches for accomplishing this. For example, a typical rapid analysis for down selection is performed and only the top m non-watchlist materials are retained and the top k watchlist materials such that the total number of materials retained (m+k) can be evaluated in the desired period of time. Alternately, a threshold for each watchlist material is determined, above which the material is automatically retained independent of it's ranking relative to the full reference library and below which it is retained only if it ranks highly relative to the library. One skilled in the art will recognize that other means of preferentially retaining watchlist materials during down selection could easily be devised.

Processing block 110 discloses the watchlist is selected from multiple watchlists. The user can select between multiple watchlists that are simultaneously present on a device. Processing block 112 states wherein a watchlist can be imported from an external device or wherein the watchlist can be exported to an external device.

Processing block 114 recites performing a final analysis of the sample material using the watchlist of at least one material and the reference list of materials. Once a plurality of possible components that might be present in the sample has been determined, analysis is performed using final analysis identification algorithms. Within the context of the present invention, the plurality of components chosen to submit for final analysis will contain both watchlist and non-watchlist materials.

Processing block 116 discloses that when final analysis uses probabilistic based methods, preferred prior probabilities are provided for materials on the watchlist. Some final analysis algorithms use probabilistic based methods. Such algorithms can incorporate 'prior probabilities' and utilize Bayes theorem to determine the exclusive probability that the measured material is a representation of one library entry versus another, often termed the "posterior probability". When no extra intelligence (i.e., information beyond the measured instrument response such as color, pH, or phase of matter) information is available at the time of measurement, no prior preference exists for any particular library component (a condition often termed "flat prior" in the probability literature). As previously noted, when a watchlist has been provided by a user this is an indication that they believe a particular set of materials are more likely to be present in the sample than other sets of materials. As such, one embodiment of the current invention is to provide preferred prior probabilities for watchlist items relative to non-watchlist items when probabilistic based methods are in use.

Processing block 120 recites determining whether a spectrum of the sample material matches at least one spectrum of materials on the watchlist and on the reference list. Processing block 122 discloses that determination of whether a spectrum of the sample material matches at least one spectrum of materials on the watchlist and on the reference list utilizes a predefined threshold for the materials on the watchlist such that probability of detecting even a small amount of a material on the watchlist is maximized. Reporting thresholds for watchlist materials can be set differently than non-watchlist materials as to maximize the probability of detecting those substances.

Processing block 123 states when the final analysis does not produce an acceptable solution, then a screening test is performed on the sample material. Screening evaluates whether at least a subset of features in the measured instrument response correspond to one or more specific substances of interest. This type of assessment evaluates whether the test material appear to contain a particular substance. Screening can be used by those with a very small set of analytes of particular interest, such as narcotics, explosive, or materials of environmental concern. Screening it is not necessary to determine the identity of materials that are not in a watch list. For example, it may be important to know whether a children's toy contains lead but it is not necessary understand what type of plastic, wood, or metal are present.

Processing block 124 discloses distinguishing an identification result that contains a watchlist material. An identification result that contains a watchlist material may be distinguished with a special icon when a watchlist material has been detected. In an alternate embodiment of the current invention a message to the user, e.g., "watchlist material detected", "threat detected", etc. could also be used to convey this information to the user. In either case, the user is provided a clear indication that a "special" material has been detected. This removes subjectivity from the interpretation of the results and does not require that the user independently assess whether an identified material is of special concern.

Described above is a method that combines the broad applicability provided by identification devices (many thousands of possible identification results) with the improved detection and reporting capabilities of screening devices. Briefly, the methodology involves providing the ability for a user to tag materials and create a watchlist within a database or library. The watchlist substances are materials that the user either has reason to believe might be present in the sample or are materials of such concern that the user wants to check for them in detail even if they have no prior information to suggest that they are present. The watchlist materials are handled by the algorithms in such a way that the limit of detection for these materials is improved. Additionally, watchlist materials are treated preferentially in the device display to unambiguously indicate to the user that a material of interest has been detected.

Figure 3:
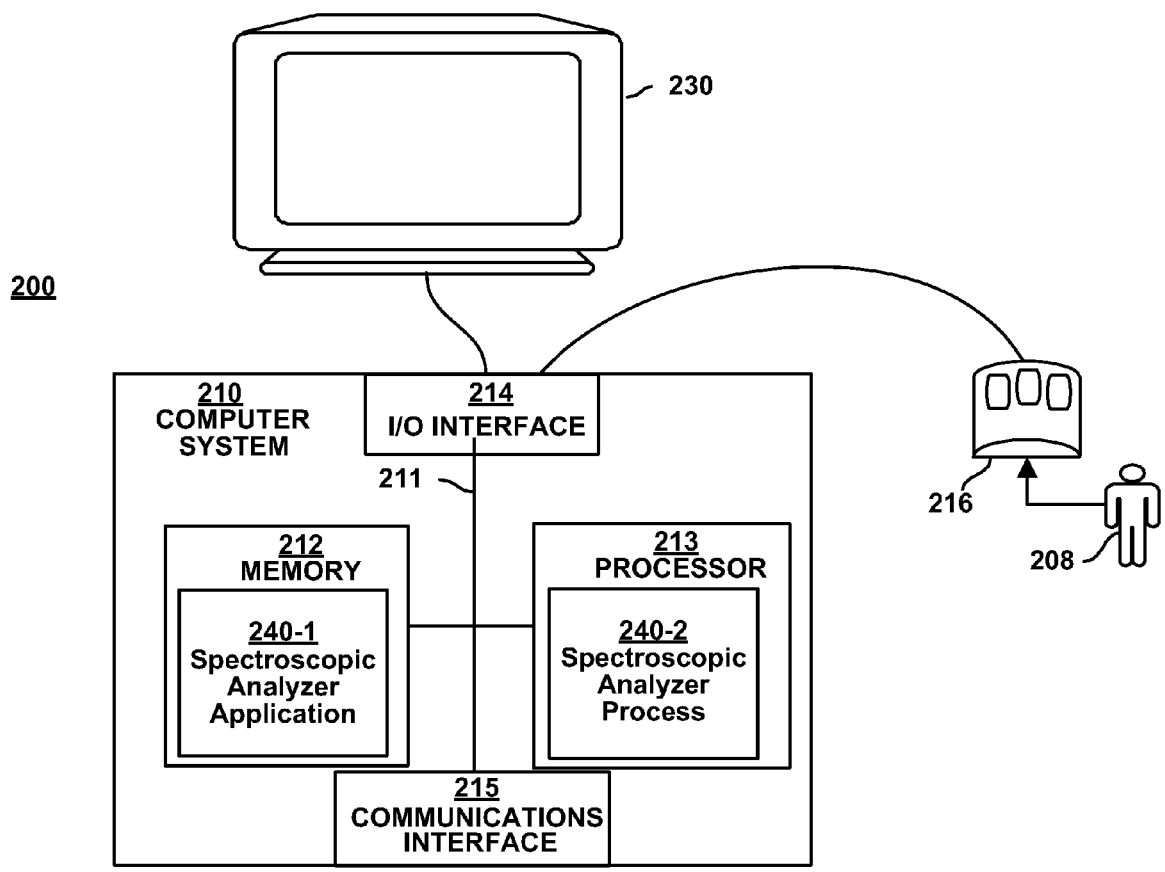
FIG. 3 illustrates an example computer system architecture for a computer system (e.g., a spectroscopic device) that allows tagging reference materials of interest in spectroscopic searching applications in accordance with embodiments of the invention.

Referring now to FIG. 3 a block diagram is shown illustrating example architecture of a computer system 210 (e.g. a spectroscopic analyzer) that executes, runs, interprets, operates or otherwise performs a application 240-1 and spectroscopic analyzer process 240-2 suitable for use in explaining example configurations disclosed herein. The computer system 210 may be any type of computerized device such as a personal computer, workstation, portable computing device, console, laptop, network terminal or the like. An input device 216 (e.g., one or more customer/developer controlled devices such as a keyboard, mouse, etc.) couples to processor 213 through I/O interface 214, and enables a customer 208 to provide input commands, and generally control the graphical customer interface that the spectroscopic analyzer application 240-1 and process 240-2 provided on the display 230. As shown in this example, the computer system 210 includes an interconnection mechanism 211 such as a data bus or other circuitry that couples a memory system 212, a processor 213, an input/output interface 214, and a communications interface 215. The communications interface 215 may also enable the computer system 210 to communicate with other devices (i.e., other computers) on a network (not shown).

The memory system 212 is any type of computer readable medium, and in this example, is encoded with a spectroscopic analyzer application 240-1 as explained herein. The spectroscopic analyzer application 240-1 may be embodied as software code such as data and/or logic instructions (e.g., code stored in the memory or on another computer readable medium such as a removable disk) that supports processing functionality according to different embodiments described herein. During operation of the computer system 210, the processor 213 accesses the memory system 212 via the interconnect 211 in order to launch, run, execute, interpret or otherwise perform the logic instructions of a spectroscopic analyzer application 240-1. Execution of a spectroscopic analyzer application 240-1 in this manner produces processing functionality in the spectroscopic analyzer process 240-2. In other words, the spectroscopic analyzer process 240-2 represents one or more portions or runtime instances of a spectroscopic analyzer application 240-1 (or the entire a spectroscopic analyzer application 240-1) performing or executing within or upon the processor 213 in the computerized device 210 at runtime.

It is noted that example configurations disclosed herein include the spectroscopic analyzer application 240-1 itself (i.e., in the form of un-executed or non-performing logic instructions and/or data). The spectroscopic analyzer application 240-1 may be stored on a computer readable medium (such as a floppy disk), hard disk, electronic, magnetic, optical, or other computer readable medium. A spectroscopic analyzer application 240-1 may also be stored in a memory system 212 such as in firmware, read only memory (ROM), or, as in this example, as executable code in, for example, Random Access Memory (RAM). In addition to these embodiments, it should also be noted that other embodiments herein include the execution of a spectroscopic analyzer application 240-1 in the processor 213 as the spectroscopic analyzer process 240-2. Those skilled in the art will understand that the computer system 210 may include other processes and/or software and hardware components, such as an operating system not shown in this example.

A display 230 need not be coupled directly to computer system 210. For example, the spectroscopic analyzer application 240-1 can be executed on a remotely accessible computerized device via the network interface 215. In this instance, the graphical customer interface 260 may be displayed locally to a customer 208 of the remote computer, and execution of the processing herein may be client-server based.

During operation, processor 213 of computer system 200 accesses memory system 212 via the interconnect 211 in order to launch, run, execute, interpret or otherwise perform the logic instructions of the spectroscopic analyzer application 240-1. Execution of spectroscopic analyzer application 240-1 produces processing functionality in spectroscopic analyzer process 240-2. In other words, the spectroscopic analyzer process 240-2 represents one or more portions of the spectroscopic analyzer application 240-1 (or the entire application) performing within or upon the processor 213 in the computer system 200.

It should be noted that, in addition to the spectroscopic analyzer process 240-2, embodiments herein include the spectroscopic analyzer application 240-1 itself (i.e., the un-executed or non-performing logic instructions and/or data).

The spectroscopic analyzer application 240-1 can be stored on a computer readable medium such as a floppy disk, hard disk, or optical medium. The spectroscopic analyzer application 240-1 can also be stored in a memory type system such as in firmware, read only memory (ROM), or, as in this example, as executable code within the memory system 212 (e.g., within Random Access Memory or RAM).

In addition to these embodiments, it should also be noted that other embodiments herein include the execution of spectroscopic analyzer application 240-1 in processor 213 as the spectroscopic analyzer process 240-2. Those skilled in the art will understand that the computer system 200 can include other processes and/or software and hardware components, such as an operating system that controls allocation and use of hardware resources associated with the computer system 200.

The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation.

References to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation.

Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where such memory may be contiguous and/or partitioned based on the application. Accordingly, references to a database may be understood to include one or more memory associations, where such references may include commercially available database products (e.g., SQL, Informix, Oracle) and also proprietary databases, and may also include other structures for associating memory such as links, queues, graphs, trees, with such structures provided for illustration and not limitation.

References to a network, unless provided otherwise, may include one or more intranets and/or the Internet, as well as a virtual network. References herein to microprocessor instructions or microprocessor-executable instructions, in accordance with the above, may be understood to include programmable hardware.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD-ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

What is claimed is:

1. A computer-implemented method comprising:
   obtaining a reference list of materials comprising spectrum data for the materials and a spectroscopic analysis of a sample comprising a plurality of unknown spectrum associated with materials in the sample;
   providing a watchlist of one or more materials of interest:
   performing a selection procedure which eliminates one or more of the spectrum data from the reference list that do not correspond to an unknown spectrum having sufficiently strong spectroscopic feature strength or do not correspond to a material of interest on the watchlist, wherein the selection procedure generates a modified reference list comprising at least one spectrum data corresponding to the materials of interest on the watchlist; and
   identifying a match between an unknown spectrum and one of the spectrum data on the modified reference list which corresponds to the materials of interest on the watchlist.

2. The method of claim 1 wherein the watchlist comprises one or more materials of interest not included on the reference list of materials.

3. The method of claim 1 wherein the materials of interest are weighted such that only a predetermined number of the materials of interest on the watchlist are considered in the selection procedure.

4. The method of claim 1 wherein the identification of the match between the unknown spectrum and the spectrum data on the modified reference list utilizes a predefined reporting threshold for the materials of interest on the watchlist such that the probability of detecting even a small amount of a material of interest on the watchlist is maximized.

5. The method of claim 1 wherein when the step of identifying uses probabilistic based methods, preferred prior probabilities are provided for materials of interest on the watchlist.

6. The method of claim 1 wherein when the step of identifying does not produce an acceptable solution, then a screening test on the sample material is performed.

7. The method of claim 1 further comprising providing an identification result to a user that contains an indication that the sample includes a material which matches a watchlist material of interest.

8. The method of claim 1 wherein the watchlist is selected from multiple watchlists.

9. The method of claim 1 wherein a watchlist can be imported from an external device or wherein the watchlist can be exported to an external device.

10. The method of claim 1 wherein scan settings are based on known spectral characteristics for materials of interest on the watchlist.

11. The method of claim 1 wherein when an unknown spectrum of a sample does not match at least one spectrum data on the modified reference list, then the method further comprises performing additional scans at the same or different scan settings.

12. The computer-implemented method of claim 1, wherein the spectrum data on the reference list of materials comprises a compressed form of data.

13. The computer-implemented method of claim 1, wherein the unknown spectrum of the sample material matches spectrum data that comprises one or more pure reference spectra or combination of reference spectra.

14. The computer-implemented method of claim 1, wherein the watchlist is provided by a user.

15. The computer-implemented method of claim 1, wherein the unknown spectrum matched to the spectrum data on the modified reference list comprises insufficiently strong spectroscopic feature strength for retention by the selection procedure, wherein the selection procedure retained the unknown spectrum on the modified reference list due to the correspondence of the unknown spectrum to the materials of interest on the watchlist.

16. A non-transitory computer readable storage medium having computer readable code thereon for tagging reference materials of interest in spectroscopic searching applications, the medium including instructions in which a computer system performs operations comprising:
obtaining a reference list of materials comprising spectrum data for the materials and a spectroscopic analysis of a sample comprising a plurality of unknown spectrum associated with materials in the sample;
providing a watchlist of one or more materials of interest;
performing a selection procedure which eliminates one or more of the spectrum data from the reference list that do not correspond to an unknown spectrum having sufficiently strong spectroscopic feature strength or do not correspond to a material of interest on the watchlist, wherein the selection procedure generates a modified reference list comprising at least one spectrum data corresponding to the materials of interest on the watchlist; and
identifying a match between an unknown spectrum and one of the spectrum data on the modified reference list which corresponds to the materials of interest on the watchlist.

17. The non-transitory computer readable storage medium of claim 16 wherein the watchlist comprises one or more materials of interest not included on the reference list of materials.

18. The non-transitory computer readable storage medium of claim 16 wherein the materials of interest are weighted such that only a predetermined number of materials of interest on the watchlist are considered in the selection procedure.

19. The non-transitory computer readable storage medium of claim 16 wherein the identification of the match between the unknown spectrum and the spectrum data on the modified reference list utilizes a predefined reporting threshold for the materials of interest on the watchlist such that the probability of detecting even a small amount of a material of interest on the watchlist is maximized.

20. The non-transitory computer readable storage medium of claim 16 wherein when the step of identifying uses probabilistic based methods, preferred prior probabilities are provided for materials of interest on the watchlist.

21. The non-transitory computer readable storage medium of claim 16 wherein when the step of identifying does not produce an acceptable solution, then a screening test on the sample material is performed.

22. The non-transitory computer readable storage medium of claim 16 further comprising providing an identification result to a user that contains an indication that the sample includes a material which matches a watchlist material of interest.

23. The non-transitory computer readable storage medium of claim 16 wherein the watchlist is selected from multiple watchlists.

24. The non-transitory computer readable storage medium of claim 16 wherein a watchlist can be imported from an external device or wherein the watchlist can be exported to an external device.

25. The non-transitory computer readable storage medium of claim 16 wherein scan settings are based on known spectral characteristics for materials of interest on the watchlist.

26. The spectrometer of claim 25 wherein the materials of interest are weighted such that only a predetermined number of materials of interest are considered in the selection procedure and wherein the identification of the match between the unknown spectrum and the spectrum data on the modified reference list utilizes a predefined threshold for the materials of interest on the watchlist such that detection of even a small amount of a material of interest on the watchlist is reported.

27. The spectrometer of claim 25, wherein the unknown spectrum matched to the spectrum data on the modified reference list comprises insufficiently strong spectroscopic feature strength for retention by the selection procedure, wherein the selection procedure retained the unknown spectrum on the modified reference list due to the correspondence of the unknown spectrum to the materials of interest on the watchlist.

28. The non-transitory computer readable storage medium of claim 16 wherein when an unknown spectrum of a sample does not match at least one spectrum data on the modified reference list, then the method further comprises performing additional scans at the same or different scan settings.

29. The non-transitory computer readable storage medium of claim 16, wherein the spectrum data on the reference list of materials comprises a compressed form of data.

30. The non-transitory computer readable storage medium of claim 16, wherein the unknown spectrum of the sample material matches spectrum data that comprises one or more pure reference spectra or combination of reference spectra.

31. The non-transitory computer readable storage medium of claim 16, wherein the watchlist is provided by a user.

32. The non-transitory computer readable storage medium of claim 16, wherein the unknown spectrum matched to the spectrum data on the modified reference list comprises insufficiently strong spectroscopic feature strength for retention by the selection procedure, wherein the selection procedure retained the unknown spectrum on the modified reference list due to the correspondence of the unknown spectrum to the materials of interest on the watchlist.

33. A spectrometer comprising:
a memory;
a processor;
a communications interface;
an interconnection mechanism coupling the memory, the processor and the communications interface; and
wherein the memory is encoded with an application providing tagging reference materials of interest in spectroscopic searching applications, that when performed on the processor, provides a process for processing information, the process causing the computer system to perform the operations of:
obtaining a reference list of materials comprising spectrum data for the materials and a spectroscopic analysis of a sample comprising a plurality of unknown spectrum associated with materials in the sample;

providing a watchlist of one or more materials of interest;

performing a selection procedure which eliminates one or more of the spectrum data from the reference list that do not correspond to an unknown spectrum having sufficiently strong spectroscopic feature strength or do not correspond to a material of interest on the watchlist, wherein the selection procedure generates a modified reference list comprising at least one spectrum data corresponding to the materials of interest on the watchlist; and identifying a match between an unknown spectrum and one of the spectrum data on the modified reference list which corresponds to the of materials of interest on the watchlist.

\* \* \* \* \*

UNITED STATES PATENT AND TRADEMARK OFFICE
CERTIFICATE OF CORRECTION

PATENT NO. : 9,110,001 B2  
APPLICATION NO. : 13/540152  
DATED : August 18, 2015  
INVENTOR(S) : Robert L. Green et al.

It is certified that error appears in the above-identified patent and that said Letters Patent is hereby corrected as shown below:

In the Claims

Column 16, line 35, In Claim 26, please replace "The spectrometer of claim 25" with -- The non-transitory computer readable storage medium of claim 25 --.

Column 16, line 43, In Claim 27, please replace "The spectrometer of claim 25" with -- The non-transitory computer readable storage medium of claim 25 --.

Column 18, line 16, In Claim 33, please replace "to the of materials" with -- to the materials --.

Signed and Sealed this  
Seventeenth Day of May, 2016

Michelle K. Lee  
*Director of the United States Patent and Trademark Office*